United States Patent
Greiser

(10) Patent No.: US 11,647,897 B2
(45) Date of Patent: May 16, 2023

(54) HANDLE FOR ENDOSCOPE, ENDOSCOPE HAVING SUCH HANDLE AND METHOD FOR DISPOSING SUCH HANDLE ON AN ENDOSCOPE

(71) Applicant: ATMOS MedizinTechnik GmbH & Co. KG, Lenzkirch (DE)

(72) Inventor: Maik Greiser, Waldshut-Tiengen (DE)

(73) Assignee: ATMOS MedizinTechnik GmbH & Co. KG, Lenzkirch (DE)

( * ) Notice: Subject to any disclaimer, the term of this patent is extended or adjusted under 35 U.S.C. 154(b) by 119 days.

(21) Appl. No.: 17/099,217

(22) Filed: Nov. 16, 2020

(65) Prior Publication Data
US 2021/0145255 A1 May 20, 2021

(30) Foreign Application Priority Data

Nov. 20, 2019 (EP) .................................. 19 210433

(51) Int. Cl.
*A61B 1/005* (2006.01)
*A61B 1/00* (2006.01)

(52) U.S. Cl.
CPC ........ *A61B 1/0052* (2013.01); *A61B 1/00045* (2013.01); *A61B 1/00066* (2013.01); *A61B 1/00105* (2013.01); *A61B 1/00163* (2013.01)

(58) Field of Classification Search
CPC ............ A61B 1/00045; A61B 1/00066; A61B 1/00105; A61B 1/0051; A61B 1/0052
See application file for complete search history.

(56) References Cited

U.S. PATENT DOCUMENTS

| | | | | |
|---|---|---|---|---|
| 4,919,112 | A | * | 4/1990 | Siegmund ............ A61B 1/0052 600/146 |
| 5,088,819 | A | | 2/1992 | Storz |
| 6,500,115 | B2 | | 12/2002 | Krattiger et al. |
| 7,658,708 | B2 | * | 2/2010 | Schwartz .......... A61M 16/0418 600/141 |
| 8,764,638 | B2 | | 7/2014 | Schwartz et al. |
| 2010/0095969 | A1 | * | 4/2010 | Schwartz ............ A61B 1/00137 128/207.14 |

FOREIGN PATENT DOCUMENTS

| | | |
|---|---|---|
| DE | 3943403 | 7/1991 |
| DE | 19839188 | 3/2000 |
| JP | 2004358012 | 12/2004 |
| WO | WO2010044862 | 4/2010 |

OTHER PUBLICATIONS

European Patent Office, Search Report, dated Jun. 3, 2020.

* cited by examiner

*Primary Examiner* — Aaron B Fairchild
(74) *Attorney, Agent, or Firm* — Akerman LLP; Peter A. Chiabotti

(57) ABSTRACT

Provided are a handle for an endoscope comprising an endoscope housing and a lens tube and wherein on the endoscope housing at least one operating element for changing a setting of the endoscope is provided, wherein the handle comprises a receiving section for receiving and retaining the endoscope and a grip section connected with the receiving section for retaining the endoscope, in which the handle further comprises at least one manipulator for operating the operating element when the handle is disposed on the endoscope, wherein the manipulator is movable relative to the receiving section and relative to the grip section, an endoscope with such a handle and a method for disposing such a handle on an endoscope.

18 Claims, 5 Drawing Sheets

HANDLE FOR ENDOSCOPE, ENDOSCOPE HAVING SUCH HANDLE AND METHOD FOR DISPOSING SUCH HANDLE ON AN ENDOSCOPE

CROSS-REFERENCE TO RELATED APPLICATIONS

This application claims priority to European Patent Application No. 19 210433.9, filed Nov. 20, 2019, which is incorporated by reference in its entirety.

SUMMARY

Endoscopy is a diagnostic and/or treatment method especially widely employed in the field of medicine, in which a lens tube, that can in particular be implemented as a rigid shaft or as a flexible tube, of an endoscope is inserted into and/or is guided through a lumen. At the distal end of the lens tube the endoscope head is disposed which can comprise, for example, an illumination device and an optical system or a camera. At the proximal end of the lens tube the endoscope housing is located, in the interior volume of which are disposed, for example, means for data and/or image processing, an electronic control, elements of the power supply and/or further optical components, in particular an eyepiece. In many cases, additional operating elements for the endoscope can be found on the endoscope housing. In particular, an operating element for pivoting the endoscope head is provided in many endoscopes which can be implemented, in particular, as a control lever.

As a rule, the operator of the endoscope must stably support the endoscope on the endoscope housing during the entire endoscopy and guide it through suitable, precise and smooth movements. This can prove to be very tiring especially during prolonged examinations or treatments since the ergonomics of commercially available endoscope housings are often inadequate, which then leads to negative effects regarding the precision achieved by the operator.

In many cases in which the endoscope remains at a specific site of the lumen substantially stationarily over a prolonged period of time, which is especially the case during endoscopic interventions, to prevent these problems it is known to provide holding devices that support the endoscope housing independently and by itself such that the operator can concentrate on the execution of the intervention.

It is also already known to secure an ergonomically more favorable handle later on the endoscope housing, that facilitates holding the endoscope by the operator. However, such displacement of the grip position entails the disadvantage that the operating elements of the endoscope are no longer easy to operate since at the manufacturer's end their position had been optimized for a different hand position of the operator.

The application addresses the problem of providing a handle for an endoscope, an endoscope with such a handle and a method for the disposition of such a handle on an endoscope that permits the ergonomically advantageous handling of an endoscope and the operation of the operating elements. This problem is resolved through a handle for an endoscope, an endoscope, and a method having the features and structures recited herein.

The handle for an endoscope is laid out for an endoscope that comprises an endoscope housing and a lens tube. The further components of the endoscope are preferably disposed in known manner in the interior of the endoscope housing and of the lens tube.

For the intended employment of the handle, on the endoscope housing at least one operating element for changing a setting of the endoscope is provided. This operating element can in particular be a lever or a bracket with which an endoscope head located on the distal lens tube end can be swiveled and that is realizable, for example, using Bowden cables guided through the lens tube.

The handle itself has a receiving section for receiving and securing the endoscope, typically of its endoscope housing, and a grip section connected with the receiving section for the operator to hold the endoscope.

The receiving section typically can comprise an aperture or an incompletely bordered cutout which entirely or partially encompasses the endoscope housing and whose inner contour is preferably adapted to the particular endoscope housing. The endoscope can be slid into the aperture which, in particular in the case of conically tapered endoscope housings, also allows the exact positioning of the handle on the endoscope. In the case of multi-part receiving sections, the handle can however also be openable in order to introduce the endoscope and subsequently be, for example, connected and closed by threaded fasteners or by locking or by being built around the endoscope. Fixing the endoscope in the receiving section does not mandatorily be brought about directly through the receiving section but rather can, for example, also be achieved by means of threaded fasteners or clamping means supported in or on the receiving section.

The handle comprises further at least one manipulator for operating the operating element when the handle is disposed on an endoscope, wherein the manipulator is movable relative to the receiving section and relative to the grip section.

Applying these measures prevents that the advantageous effect achieved by providing an ergonomically advantageous grip position that is accomplished by the handle is entirely or partially undone again thereby that the operating element of the endoscope has been disposed such that it is optimized for a different grip position and, conversely, the feasibility for actuating the operating element is offered that is ergonomically ideally adapted to the grip position provided by the handle.

The handle is preferably implemented such that it is upgradable. This is accomplished if it can be separated from the endoscope and is not unitarily formed onto the endoscope.

Of advantage is herein an overall configuration of the endoscope and handle with manipulator in the form of a pistol, in which the barrel of the pistol is formed by the endoscope received in the receiving section of the handle, the grip of the pistol is formed by the grip section of the handle and the trigger of the pistole is formed by the manipulator or by a portion of the manipulator.

Especially advantageous have been found to be handles in which the receiving section forms an angle relative to the grip section. In particular preferred is herein an angulation such that the end of the grip section, facing away from the receiving section, is tilted, especially preferably at an angle between 5° and 45°, in the direction toward the proximal end of the endoscope disposed as intended in the retaining section.

If the handle comprises means for changing the position of the receiving section relative to the grip section, the ergonomics can be individually adjusted to the operator. Such means can preferably be realized thereby that on the receiving section an oblong hole or a series of holes is provided at different positions in or on which the handle can be fixed by clamps, detents or threaded fasteners.

In an advantageous variant of the receiving section is implemented in at least two parts, with a first part and a second part, wherein the grip section and/or the manipulator is or are retained between the first part and the second part. This includes configurations in which an aperture for receiving the endoscope is only provided in one of the parts of the receiving sections; other configurations, however, can also provide that the aperture is formed as edging or delimitation of the aperture through the cooperation of several parts of the receiving sections.

This is especially simply realizable if the receiving section comprises a single-part or multipart support section on which the grip section and/or the manipulator are supported. This support section, or one of the parts forming it, can, in particular, extend from the parts of the receiving section forming the aperture for receiving the endoscope and is, to this extent, also interpretable as a feasible part of the receiving section.

If the manipulator comprises a receiver for the introduction of at least a section of the operating element of the endoscope, the connection between operating element and manipulator can be established in a simple and secure manner. In the simplest case this receiver can be formed by a hole.

In a further advantageous implementation of the manipulator, the manipulator comprises a receiver for receiving at least a portion of a finger of an operator of the endoscope, which receiver can also be formed, for example, by a hole. In comparison to a contact area, the advantage of such a receiver is that it permits the operator to apply tension as well as pressure via the manipulator without changing the position of the finger.

To ensure that the manipulator functions free of problems, it is advantageous for the manipulator to extend at least in sections in an interior volume of the handle.

An especially advantageous implementation of the manipulator is given when the manipulator comprises a first section and a second section, wherein the first section is rotatable relative to the second section about a first rotational axis and wherein the second section is rotatable relative to the receiving section and/or relative to the grip section about a second rotational axis that extends parallel to the first rotational axis. Such a formation enables the manipulator, in particular the operator, to displace an operating element not only linearly during the operation but also move it without difficulties on a circulator path. By adapting the lever relationships of the second section, referred to the position of the second rotational axis in the second section, the desired degree of fineness of the setting can be adapted.

According to another preferred further development of the handle, it comprises a display screen receiving section for receiving a display screen. This permits equipping the endoscope with a mobile display screen, which, for example, can also be the display of a tablet PC or of a smartphone, in order to display the images obtained therewith directly or to store them and/or to forward them. The display screen can optionally also supply the endoscope with power with its power supply which, overall, leads to an especially light-weight and mobile endoscope.

The display screen receiving section can, for example, be disposed on the side, opposite the grip section, of the receiving section or laterally on the receiving section. It is advantageous if it provides a degree of freedom of motion with which the operator can individually optimize the orientation of the display screen when it is set into the display screen receiving section or into a display screen receiver of the display screen receiving section, for example through a display screen receiving section with a pivot joint or a ball and socket joint.

It is herein especially preferred for the display screen receiving section for receiving a display screen to be detachably disposed on the handle. This can be carried out, for example through reciprocal magnetic action, in particular between a magnet, disposed at the corresponding site of the receiving section or in it, and a magnet, disposed on the display screen receiving section, and/or through reciprocal mechanical action, in particular by plugging it on, snapping it on or connecting it by threaded fasteners. The connection is preferably only established after the endoscope has already been inserted into the receiving section of the handle.

The endoscope can comprise an endoscope housing and a lens tube, wherein on the endoscope housing at least one operating element is located for changing a setting of the endoscope. In an especially preferred variant this operating element can in particular be a lever, preferably a bow-shaped lever with which the position of the endoscope head, disposed at the distal end of the lens tube, can be set.

The endoscope comprises a handle according to the disclosure above.

The method for disposing a handle on an endoscope with an endoscope housing, wherein on the endoscope housing at least one operating element for changing a setting of the endoscope is provided, and with a lens tube, is implemented with a handle that comprises a receiving section for receiving and retaining the endoscope, a grip section connected with the receiving section—preferably but not mandatorily such as to be detachable—for retaining the endoscope and at least one manipulator for operating the operating element of the endoscope, wherein this manipulator is movable relative to the receiving section and relative to the grip section. The method comprises in particular the steps receiving the endoscope in an aperture in the receiving section of the handle, and connecting the operating element with the manipulator.

Receiving the endoscope can be carried out thereby that the endoscope is slid into the aperture or that the receiving section is implemented as a multipart section such that it can be built entirely or partially about the endoscope or, for example, also thereby that the endoscope is secured using threaded fasteners or clamping means on the receiving section.

In a preferred further development of the method the manipulator, while it is being connected with the operating element, is detached from the handle and, after the connection with the operating element, is again or for the first time secured on the handle. This permits optimizing, independently of one another, the connection between receiving section and endoscope on the one hand and, on the other hand, that between manipulator and operating element.

The method can be implemented especially advantageously if a handle is utilized that has a manipulator which comprises a first section and a second section, wherein the first section is rotatable about a first rotational axis relative to the second section and wherein the second section is rotatable relative to the receiving section and/or relative to the grip section about a second rotational axis that extends parallel to the first rotational axis. The operating elements is subsequently connected with the manipulator thereby that the operating element is introduced into a receiving aperture provided on the first section of the manipulator.

The manipulator connected in this manner with the operating element is placed into a channel in the receiving section and connected across the second rotational axis with the receiving section. This can be accomplished, for example, thereby that the manipulator is emplaced onto the second rotational axis already provided on the receiving section or thereby that a second rotational axis connected with the manipulator is inserted into a bore provided on the receiving section or a support provided on the receiving section.

It is herein especially preferred for the channel, after the manipulator connected with the operating elements has been emplaced and after the connection across the second rotational axis with the receiving section, to be closed using a cover, which can, for example, be latched onto it or by being connected using threaded fasteners.

An advantageous variant of the method provides that a handle is utilized which has a display screen receiving section and that a display screen is disposed in the display screen receiving section and at least a signal communication is established with the endoscope, for example via a connection cable between display screen and endoscope, such that on the display screen, which can be, for example, the display of a smartphone or of a tablet PC that is disposed in the display screen receiving section, the visual data obtained with the endoscope are displayed directly. A highly mobile endoscope system can be provided in this manner which is still further optimized if the connection across the connection cable enables also the power supply of the endoscope by the power supply, in particular through a battery, of the display screen.

In an especially preferred further development of the method a handle is utilized which has a detachable display screen receiving section, wherein this detachable display screen receiving section is only connected with the handle after the endoscope (1) [sic] has been received in an aperture in the receiving section of the handle. It is in particular further preferred if this connection is also only established subsequent to the connection between the manipulator and the operating element. It is thereby ensured that the display screen receiver, which is often a relatively unwieldy structural component, does not present any interference during the execution of the other method steps.

BRIEF DESCRIPTION OF DRAWINGS

In the disclosure will be described in greater detail in conjunction with Figures that show an embodiment example. Therein show.

DETAILED DESCRIPTION

Figure 1:
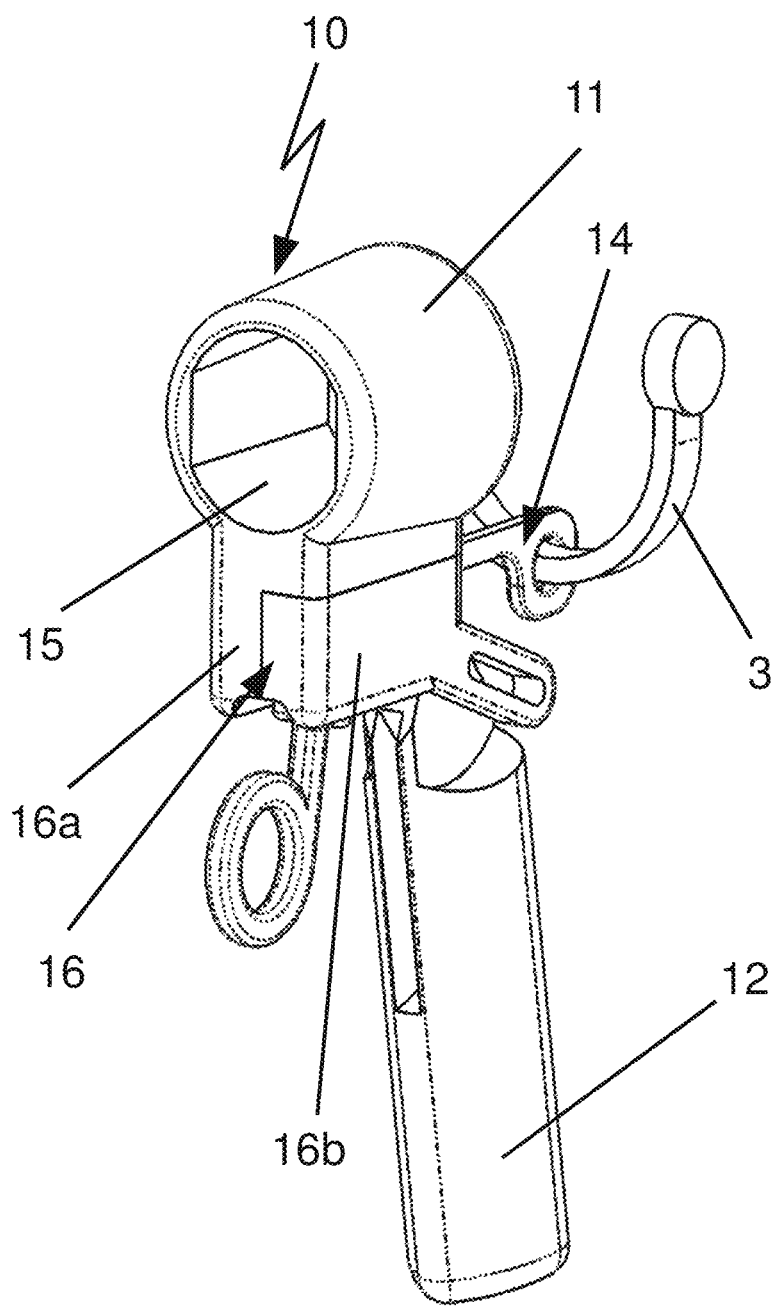
FIG. 1: an embodiment example of a handle in cooperation with an operating element of an endoscope.
Figure 2:
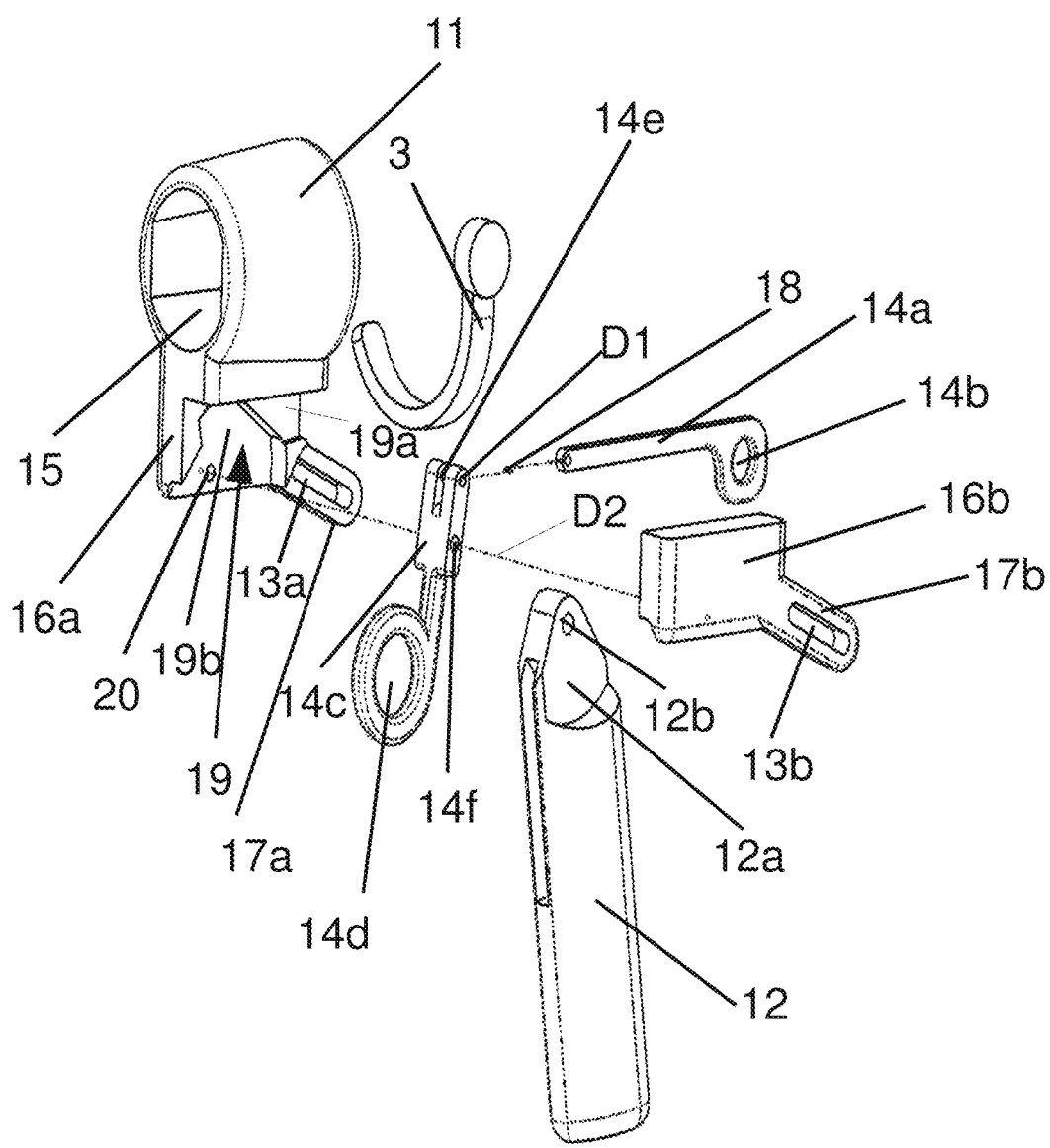
FIG. 2: an exploded view of the arrangement comprising handle and operating element of FIG. 1, FIG. 3: a side view of an endoscope with a handle as depicted in FIG. 1 in a first position of the operating element.
Figure 3:
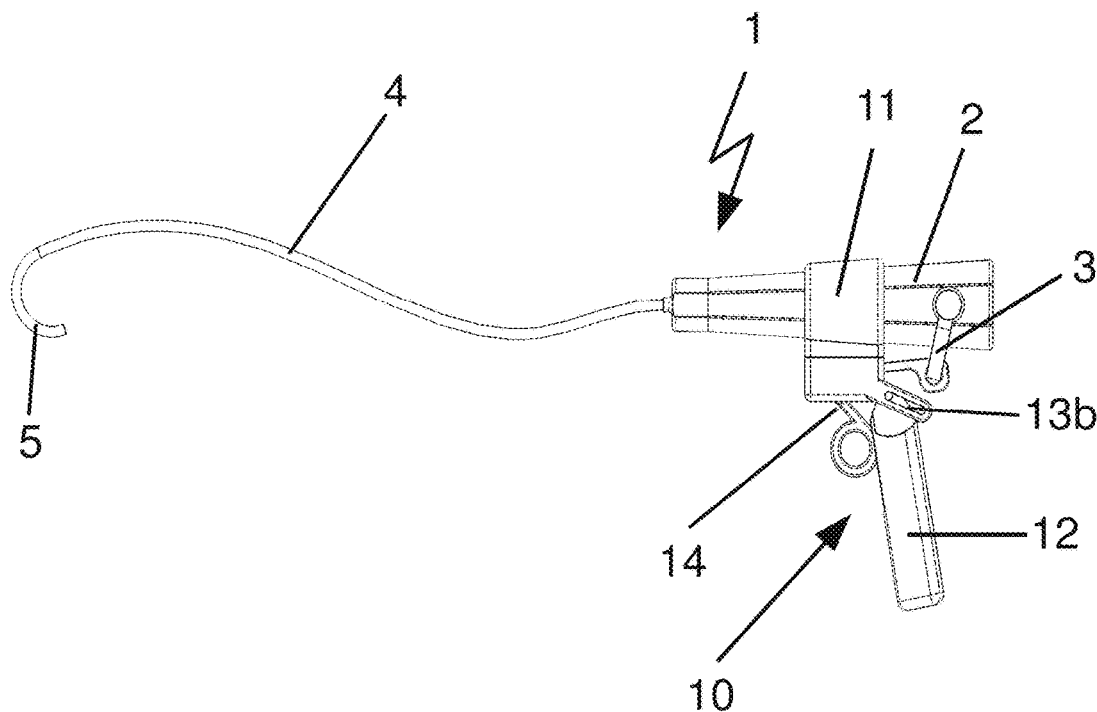
Figure 4:
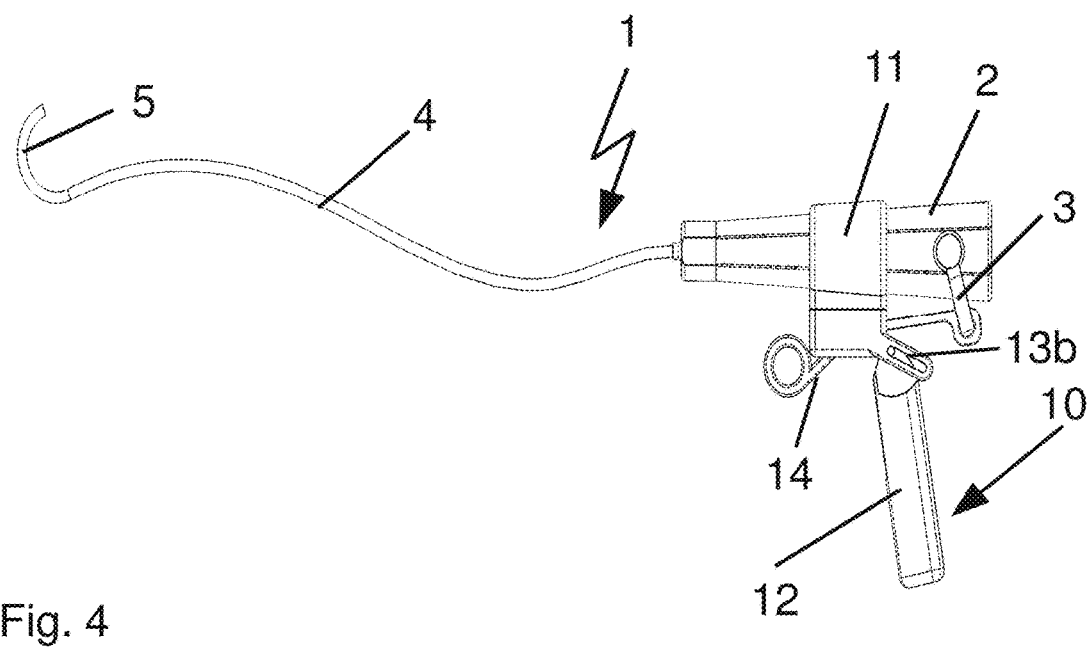
FIG. 4: a side view of an endoscope with a handle as depicted in FIG. 1 in a second position of the operating element.

FIGS. 1 and 2 show a handle 10 for an endoscope 1, not depicted in these Figures however shown by example in FIGS. 3 and 4, together with an operating element 3, here implemented by example in the form of a bow-shaped bracket, of the endoscope 3 which is actuatable across the handle 10, more specifically across a manipulator 14 disposed thereon.

The handle 10 comprises a receiving section 11 and has, further, a grip section 12 whose position is changeable relative to the receiving section 11 in oblong holes 13*a*, 13*b*, and specifically in particular also with respect to a tilt angle relative to the receiving section 11.

The manipulator 14 comprises a first section 14*a* with a receiver 14*b* for the insertion, at least of sections, of the operating element 3 and a second section 14*c* with a receiver 14*d* for the introduction, at least of portions, of a finger of an operator of the endoscope 1. As is especially clearly evident in FIG. 2, the portion of the second section 14*c*, facing the first section 14*a*, is provided with a slot 14*e* for receiving the end region, opposite to the end region of receiver 14*b*, of the first section 14*a* and here fixed with a pin 18 guided through both sections such that it is rotatable about the first rotational axis D defined by the pin 18 such that the first section 14*a* of the manipulator 14 is rotatable relative to the second section 14*b* of the manipulator [14] about the first rotational axis D1.

The receiving section 11 encompasses—in this case with a unitary edge which, however, also can be composed of several parts or segments—annularly an aperture 15 for receiving the endoscope 1. The aperture 15 is herein adapted to the shape of the endoscope housing 2 of endoscope 1. As is discernible in the representation of FIGS. 3 and 4, in this example an endoscope housing 2 tapering conically in the direction toward a lens tube 4, whose outer contours can be described as circles flattened on two opposing sides, such that the aperture 15 as a consequence of its adaption to the endoscope housing 3, has a conically tapering inner contour which can be described as circles flattened on two opposingly located sides. This defines simultaneously how far the endoscope housing 3 can be slid into the aperture 15.

Formed unitarily onto the receiving section 11 and, to this extent, interpretable as a section of the receiving section 11, is a first part 16*a* of a support section 16 which cooperates with a cover-shaped second parts 16*b*, separable from the first part 16*a* and consequently also from receiving section 11, of the support section 16.

The support section 16 serves, on the one hand, for supporting the grip section [12] between two extensions 17*a* of the first part 16*a* of support section 16 on the one hand and 17*b* of the second part 16*b* of bearing section 16 on the other hand, in which the oblong holes 13*a*, 13*b* are disposed. The grip section 12 is inserted with its connection region 12*a* such between the extensions 17*a*, 17*b* that the bore 12*b* is aligned with the oblong holes, brought into the ergonomically most favorable position for the operator by sliding and tilting and fixed, which can take place, for example, through a locking screw or by being clamped together which can be brought about by connecting the parts 16*a*, 16*b* of support section 16 using clamps, detents or threaded fasteners.

The support section 16 defines, on the other hand, through its first part 16*a* and the second part 16*b* a channel 19 for receiving subregions of manipulator 14. In a first section 19*a* of channel 19 is received a subregion of the first section 14*a* of the manipulator 14. It should be pointed out that the width b of channel 19 in section 19*a* is selected to be markedly greater than the width of the received region of section 14*a* such that the section 14*a* at different positions of the operating element 3 extends at different positions of the operating element 3 at different angles through channel 19.

It becomes thereby feasible to control an operating element 3 moved on a circular path with the manipulator 14.

In a second section 19b of channel 19 a subregion of the second section 14c of manipulator 14 is received. The support section 16 has in particular in this region a bore 20 in which the manipulator 14, for example by means of an axle, formed onto the cover-like second part 16b of support section 16 and not visible in the Figures, that is inserted through a bore 14f in the second section 14c of manipulator [14] into the bore 20, is supported such that the second section 14c of manipulator 14 is rotatable relative to the receiving section 11 about a second rotational axis D2 that extends parallel to the first rotational axis D1.

The described structure of the handle 10 in particular enables establishing separately from one another the connection between receiving section 11 and endoscope 1, or endoscope housing 2, on the one hand, and manipulator 14 and actuation element 3 on the other hand, and only subsequently to connect the manipulator 14 with the handle 10 which, for example, is required for bow-form actuation elements 3 of endoscopes whose endoscope housing does not have a rotationally symmetrical geometry and which therefore cannot be rotated in the receiving section 11.

In FIGS. 3 and 4 is evident in each instance the same endoscope 1 with endoscope housing 2, on which the operating element 3 is disposed, with lens tube 4 and with endoscope head 5. The operating element 3 serves herein, as can be seen immediately when comparing FIGS. 3 and 4, for swivelling the endoscope head 5. When the operating element 3 is at its left, in the perspective FIGS. 3 and 4, abutment the endoscope head 5 is maximally curved downward; if it is at its right, in the perspective of FIGS. 3 and 4, abutment, the endoscope head 5 is maximally curved upward.

When viewing FIGS. 3 and 4, discernible is further the handle 10, structured as described above in reference to FIGS. 1 and 2, with receiving section 11, grip section 12, whose position relative to the receiving section 11 can be changed by means of oblong hole 13 and which preferably, as can be seen in FIGS. 3 and 4, that represent an actual application situation, extends at an angle relative to the receiving section 11. On handle 10 is further evident the manipulator 14, which comprises a first section 14a with receiver 14b for the insertion of at least sections of the operating element 3 and a second section 14c with receiver 14d for the introduction of at least portions of a finger of an operator of the endoscope 1.

If the operator of endoscope 1 moves the second section 14c of manipulator 14 as far as is possible to the grip section 12, as is shown in FIG. 3, the operating element 3 is pulled to its left abutment and the endoscope head 5 is swiveled maximally downwardly. If he moves it as far as possible away from the grip section 12, the operating element 3 is shifted to its right abutment and the endoscope head 5 is swiveled maximally upwardly. The operator can accordingly with his finger introduced quite simply, with the same hand in which he holds the endoscope 1, by moving the finger over the manipulator 14 control the operating element 3 and can move the endoscope head 5 into a desired position.

Figure 5:
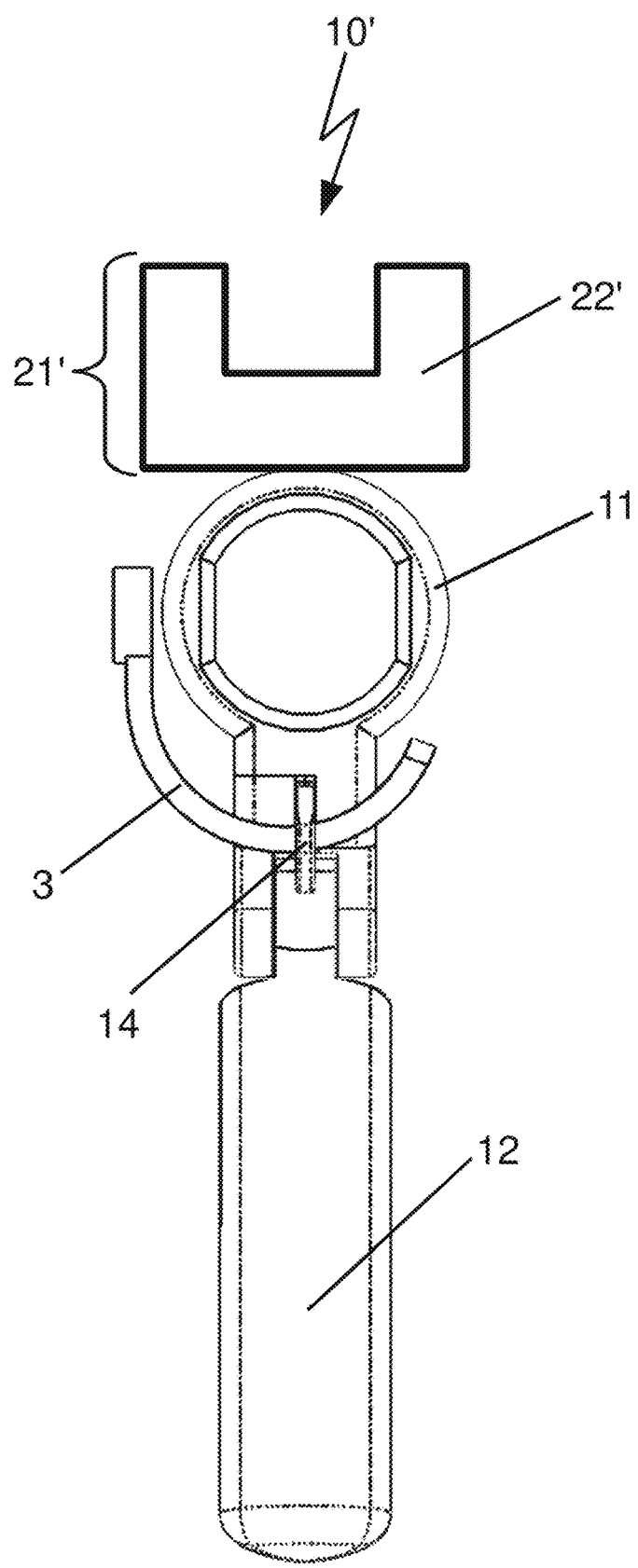
FIG. 5: a back view of a first variant of the handle of FIGS. 1 and 2, and FIG. 6: a back view of a second variant of the handle of FIGS. 1 and 2.
Figure 6:
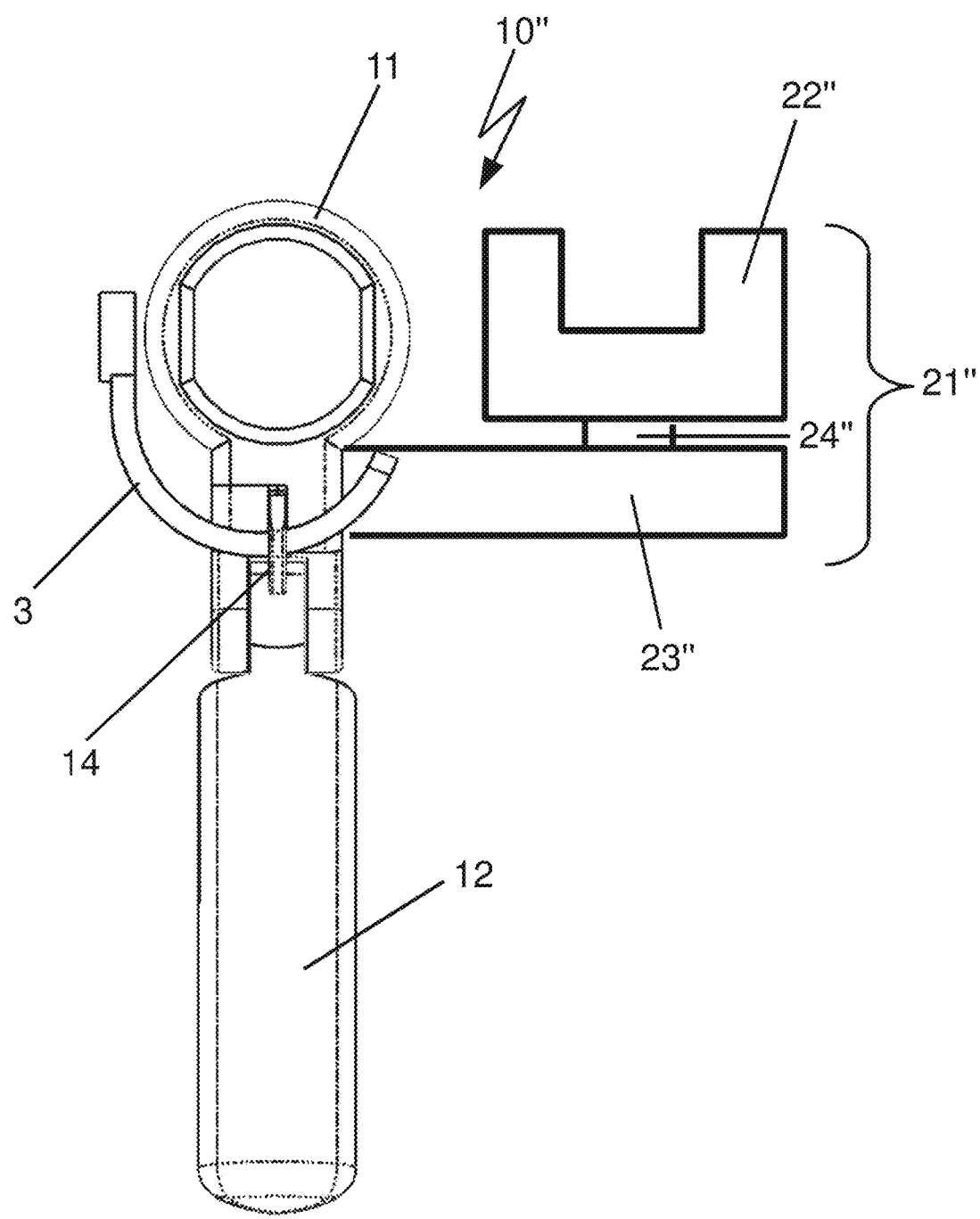

FIGS. 5 and 6 show each handles 10', 10" which represent variants of handle 10 from FIGS. 1 and 2 and only differ from handle 10 according to FIGS. 1 and 2 in that the handle comprises additionally a display screen receiving section 21' or 21", respectively. Therefore in FIGS. 5 and 6 the same reference numbers as in FIGS. 1 and 2 are used for components of the particular variant of handle 10', 10" as were already used in connection with FIGS. 1 and 2 and reference is made to the corresponding description.

The display screen receiving sections 21', 21" serve for the purpose of being able to dispose a not depicted display screen on handle 10', 10". This display screen can, in particular, also be formed by the display of a tablet PC or of a smartphone. As a rule, it is not an inherent component of the handle and/or of the endoscope 1 and is brought at least into data communication with the endoscope 1 in order to enable the visual data obtained with the endoscope 1 to be displayed directly to the operator. If this data communication with the endoscope 1 takes place through a wired connection between endoscope 1 and display screen, the endoscope 1 can also be provided with power required for its operation across this wired connection, which power can subsequently be provided through the power supply, in particular a battery, of the display screen.

The display screen receiving section 21' depicted in FIG. 5 is simply comprised of a display screen retainer 22", which is schematically simply depicted as U-shaped, wherein the limbs of the U-shaped display screen retainer 22' comprise each in the perspectives of FIG. 5 a non-visible receiving slot into which the display screen is inserted and optionally can be fixed preferably with fixing means or by a clamping effect between the inner faces of the wall of the receiving slot.

The display screen receiving section 21' is disposed on the side, opposite the grip section 12, of the receiving section 11 and is preferably detachably connected with the receiving section 11. This can be accomplished for example through magnetic interaction, in particular between a magnet disposed at the corresponding site of the receiving section 11 thereon or therein and a magnet disposed on the display screen receiving section 21', and/or through mechanical interaction, in particular by forming it through connections using emplacement, detents or threaded fasteners. The connection is preferably only established after the endoscope 1 has already been inserted into the receiving section 11 of the handle 10'.

The display screen receiving section 21" depicted in FIG. 6 also comprises a display screen retainer 22" which is schematically simply depicted in the form of a U.

The limbs of the U-shaped display screen retainer 22" also comprise each a receiving slot, not visible in the perspective of FIG. 6, into which the display screen can be inserted and optionally be fixed preferably using fixing means or by clamping effects between the inner wall faces of the receiving slot. In the display screen receiving section 21" the display screen retainer 22" is however connected with a support arm 22" across a pivot joint 24".

The display screen receiving section 21" in the embodiment example shown in FIG. 6 is disposed laterally on the receiving section 11, for example at its support section 16, and, like the display screen receiving section 21', is preferably detachably connected with the receiving section 11 or the support section 16. This is here also accomplished, for example, by magnetic interaction, in particular between a magnet disposed at the corresponding site of the receiving section 11 on or in the latter and a magnet disposed on the display screen receiving section 21' and/or through mechanical interaction, in particular by connection using emplacement, detents or threaded fasteners. The connection is in this case also preferably only established after the endoscope 1 has already been inserted into the receiving section 11 of handle 10".

LIST OF REFERENCE SYMBOLS

1 Endoscope
2 Endoscope housing

3 Operating element
4 Lens tube
5 Endoscope head
10, 10', 10" Handle
11 Receiving section
12 Grip section
12a Connection region
12b Bore
13a, 13b Oblong hole
14 Manipulator
14a First section
14b Receiver
14c Second section
14d Receiver
14e Slot
14f Bore
15 Aperture
16 Support section
16a First part
16b Second part
17a, 17b Extension
18 Pin
19 Channel
19a First section
19b Second section
20 Bore
21', 21" Display screen receiving section
22', 22" Retainer
23" Support arm
24" Pivot joint
b Width
D1 First rotational axis
D2 Second rotational axis

The invention claimed is:

1. An endoscope handle, comprising:
a cylindrical section with an aperture narrowing distally and that is configured to receive an endoscope,
a grip section connected with the cylindrical section,
a manipulator, comprising:
　a trigger pullable toward the grip section and pivotable within a support section below the cylindrical section;
　a linkage having an endoscope operating lever receiving aperture, the linkage attached directly to and configured to be actuated by the trigger to advance and retreat along a longitudinal direction of the aperture of the cylindrical section, thereby manipulating an operating lever of the endoscope after the cylindrical section has been disposed on the endoscope,
wherein the manipulator is movable relative to the cylindrical section and relative to the grip section.

2. The endoscope handle as in claim 1, further comprising a channel for changing a position of the cylindrical section relative to the grip section.

3. The endoscope handle as in claim 1, wherein the cylindrical section comprises two parts with a first receiving section part and a second receiving section part and wherein the grip section, the manipulator, or both the grip section and manipulator, are retained between the first receiving section part and the second receiving section part.

4. The endoscope handle as in claim 1, wherein the cylindrical section comprises a one- or multi-part support section on which the grip section, the manipulator, or both the grip section and the manipulator, are supported.

5. The endoscope handle as in claim 1, wherein the manipulator has a first manipulator receiver for the insertion of at least sections of the endoscope operating lever.

6. The endoscope handle as in claim 1, wherein the manipulator comprises a second manipulator receiver for introduction of at least portions of a finger of an operator of the endoscope.

7. The endoscope handle as in claim 1, wherein the manipulator extends at least in sections in an interior volume of the handle.

8. The endoscope handle as in claim 1, wherein the manipulator comprises a first manipulator section and a second manipulator section, wherein the first manipulator section is rotatable about a first rotational axis relative to the second manipulator section, and
　wherein the second manipulator section is rotatable relative to the cylindrical section, the grip section, or both the cylindrical section and the grip section, about a second rotational axis,
　wherein the second rotational axis extends parallel to the first rotational axis.

9. The endoscope handle as in claim 1, wherein the manipulator is reversibly separable from the handle and securable again on the handle.

10. The endoscope handle as in claim 1, wherein the handle comprises a display screen mount.

11. The endoscope handle as in claim 10, wherein the display screen receiving section is detachably disposed on the handle.

12. The endoscope handle as in claim 1, further comprising:
　an endoscope housing having a lens tube and the endoscope operating lever for changing a setting of the endoscope.

13. A method for disposing a handle on an endoscope with an endoscope housing having a lens tube and an endoscope operating lever for changing a setting of the endoscope comprising:
　providing an endoscope handle, comprising:
　　a cylindrical section with an aperture narrowing distally and that is configured to receive the endoscope,
　　a grip section connected with the cylindrical section,
　　a manipulator, comprising:
　　　a trigger pullable toward the grip section and pivotable within a support section below the cylindrical section,
　　　a linkage having an endoscope operating lever receiving aperture, the linkage attached directly to and configured to be actuated by the trigger to advance and retreat along a longitudinal direction of the aperture of the cylindrical section, thereby manipulating an operating lever of the endoscope after the cylindrical section has been disposed on the endoscope,
　　wherein the manipulator is movable relative to the cylindrical section and relative to the grip section;
　receiving the endoscope in the aperture of the cylindrical section; and
　connecting the endoscope lever with the manipulator.

14. The method as in claim 13, wherein while the manipulator is being connected with the endoscope operating lever is detached from the handle and, after the connection with the endoscope operating lever, is again or for the first time secured on the handle.

15. The method as in claim 14, wherein the manipulator comprises a first manipulator section and a second manipulator section, wherein the first manipulator section is rotatable relative to the second manipulator section about a first rotational axis, wherein the second manipulator section is rotatable relative to the cylindrical section, the grip section, or both the cylindrical section and the grip section, about a second rotational axis that extends parallel to the first rotational axis, wherein the endoscope operating lever is connected with the manipulator such that the endoscope operating lever is inserted into a first manipulator receiving section provided on the first section of the manipulator, wherein the manipulator is placed into an interior channel in the cylindrical section and is connected across a structural element that connects the second rotational axis with the cylindrical section.

16. The method as in claim 15, wherein the inner channel is closed with a cover after the manipulator connected with the endoscope operating lever has been emplaced and after the connection across the second rotational axis with the cylindrical section has been established.

17. The method as in claim 13, wherein the endoscope handle has a display screen mount and at least one signal communication is established with the endoscope.

18. The method as in claim 13, wherein the endoscope handle has a detachable display screen receiving section that is only connected with the endoscope handle after the endoscope has been received in an aperture in the receiving section of the endoscope handle.

* * * * *